(12) United States Patent
Chang et al.

(10) Patent No.: US 8,865,665 B2
(45) Date of Patent: Oct. 21, 2014

(54) AMINOGLYCOSIDES: SYNTHESIS AND USE AS ANTIFUNGALS

(75) Inventors: Cheng-Wei T. Chang, Logan, UT (US); Jon Takemoto, North Logan, UT (US)

(73) Assignee: Utah State University, Logan, UT (US)

( * ) Notice: Subject to any disclaimer, the term of this patent is extended or adjusted under 35 U.S.C. 154(b) by 21 days.

(21) Appl. No.: 13/316,720

(22) Filed: Dec. 12, 2011

(65) Prior Publication Data

US 2012/0316125 A1     Dec. 13, 2012

Related U.S. Application Data

(60) Provisional application No. 61/422,983, filed on Dec. 14, 2010.

(51) Int. Cl.

| | | |
|---|---|---|
| *C07H 15/234* | (2006.01) | |
| *A61K 31/7036* | (2006.01) | |
| *A01N 43/16* | (2006.01) | |
| *C07H 13/06* | (2006.01) | |
| *C07H 5/06* | (2006.01) | |
| *C07H 15/22* | (2006.01) | |
| *C07H 11/00* | (2006.01) | |

(52) U.S. Cl.
CPC .............. *C07H 15/234* (2013.01); *C07H 13/06* (2013.01); *C07H 5/06* (2013.01); *A61K 31/7036* (2013.01); *C07H 15/22* (2013.01); *A01N 43/16* (2013.01); *C07H 11/00* (2013.01)
USPC .......................................................... 514/41

(58) Field of Classification Search
CPC ... C07H 15/234; A61K 31/7036; A01N 43/16
See application file for complete search history.

(56) References Cited

U.S. PATENT DOCUMENTS

| 4,279,997 A | 7/1981 | Oka et al. |
| 4,493,831 A | 1/1985 | Takaya et al. |
| 5,039,666 A | 8/1991 | Novick et al. |
| 2011/0130357 A1 | 6/2011 | Chang et al. |

FOREIGN PATENT DOCUMENTS

| CN | 101481397 A | * | 7/2009 | ......... A61K 31/7036 |
| WO | WO 2004050677 A1 | * | 6/2004 | ......... A61K 31/7036 |
| WO | 2005/116041 A2 | | 12/2005 | |
| WO | WO 2005116041 | | 12/2005 | |
| WO | 2009/152202 A2 | | 12/2009 | |

OTHER PUBLICATIONS

Li et al. Novel kanamycin A derivative, and preparation and use thereof, CN 101481397 A, Jul. 15, 2009, machine translation, Retreived on May 30, 2013 from http://worldwide.espacenet.com.*
Mingeot-Leclercq, M. P., Van Schepdael, A., Brasseur, R., Busson, R., Vanderhaeghe, H. J., Claes, P. J., & Tulkens, P. M. (1991). New derivatives of kanamycin B obtained by modifications and substitutions in position 6. Journal of medicinal chemistry, 34(4), 1476-1482.*
Wang, J., & Chang, C. W. T. Design, Chemical Synthesis, and Antibacterial Activity of Kanamycin and Neomycin Class Aminoglycoside Antibiotics (Ch. 4, pp. p141-180), In: Arya, D. P. (2007). Aminoglycoside antibiotics: from chemical biology to drug discovery (vol. 5). Wiley. com.*
PCT/US2011/064481; filed Dec. 12, 2011; Utah State University et al; international search report mailing date Sep. 12, 2012.
Wang, J. et al.; "Glycodiversification for the Optimization of Kanamycin Class Aminoglycodides"; J. Med. Chem . . , 2005, vol. 48, pp. 6271-6285.
Schepdael et al., New derivatives of kanamycin B obtained by modifications and substitutions in position 6".1. Synthesis and microbiological evaluation, 34 J. Med. Chem. 1468-1476 (1991).
Chang et al.; Antibacterial to Antifungal Conversion of Neamine Aminoglycosides Through Alkyl Modification. Strategy for Reviving Old Drugs into Agrofungicides; The Journal of Antibiotics; 2010; pp. 1-6.
Wang, J. et al., Glycodiversification for the Optimization of the Kanamycin Class Aminoglycosides, J. Med. Chem., Apr. 19, 2005, vol. 48, pp. 6271-6285.
International Search Report and Written Opinion for PCT/US2011/064481, Dated Sep. 12, 2012.

* cited by examiner

*Primary Examiner* — Shaojia Anna Jiang
*Assistant Examiner* — Dale R Miller

(57) ABSTRACT

The present invention relates to novel aminoglycoside analogs having certain substituents at the 6 position of ring III which exhibit improved antifungal activity but possess minimal antibacterial properties. The compounds of the present invention are analogues of kanamycin A. Also provided are methods of synthesizing and methods of using the compounds of the present invention. The compounds of the present invention are useful in treating or preventing fungal disease.

18 Claims, No Drawings

AMINOGLYCOSIDES: SYNTHESIS AND USE AS ANTIFUNGALS

RELATED APPLICATIONS

This application claims the benefit of U.S. Provisional Application No. 61/422,983, filed Dec. 14, 2010, entitled New Aminoglycosides: Synthesis and Use as Antifungals" which is incorporated herein in its entirety by this reference.

REFERENCE TO SEQUENCE LISTING, A TABLE, OR A COMPUTER PROGRAM LISTING COMPACT DISK APPENDIX

Not Applicable

TECHNICAL FIELD

The present invention is in the technical field of antimicrobials. More particularly, the present invention is in the technical field of aminoglycoside antimicrobials and antifungals in particular.

BACKGROUND

Aminoglycoside antibiotics have been commonly used as a medical treatment against infectious diseases for over 60 years, although the prevalence of aminoglycoside resistant bacteria has significantly reduced their effectiveness. Aminoglycosides have two or more amino sugars bound to an aminocyclitol ring through glycosidic bonds. Naturally occurring aminoglycosides (produced by Actinomycetes) are widely used as antibiotics against bacterial infections of animals and humans. These include the well-known antibiotics kanamycin, streptomycin and neomycin. Aminoglycoside antibiotics are believed to act on the bacterial protein synthesis machinery, leading to the formation of defective cell proteins.

In medicine, fungal diseases have emerged over the last 25 years as a major public health problem. Among the prominent reasons for this increase are the lack of efficacious antifungal agents, increases in immunocompromised conditions (e.g., organ transplants and HIV/AIDS), and widespread resistance to the most commonly used antifungals. The strongest medically used antifungal agent, amphotericin B, is an effective medication, but is also highly toxic to patients. The toxicity levels of the available antifungal medications are a common concern for medical practitioners. U.S. Pat. No. 5,039,666 to Novick, Jr. (1991) shows an aminoglycoside compound "gentamicin" having reduced nephrotoxicity induced by the aminoglycoside. Other common antifungal medications are used to treat infections such as athlete's foot, ringworm, candidiasis (thrush) and serious systemic infections such as cryptococcal meningitis, and others.

In agriculture, the control of crop diseases by direct application of biocides remains the most effective and most widely used strategy. Nevertheless, concerns with inconsistent and declining effectiveness, environmental impacts, animal/human toxicity, and costs continue to challenge the use of existing biocides. Traditionally, aminoglycosides have been developed and used as antibiotics against bacteria. A recent report, however, suggests inhibition of plant pathogenic fungi (particularly by paramomycin) by traditional and natural aminoglycosides. One specific example of a crop pathogen is *Fusarium graminearum*, the most common causative agent of head blight disease in wheat and barley in North America. Infection with *F. graminearum* is difficult to predict and can result in catastrophic crop loss.

Kanamycin is a known aminoglycoside antibiotic. The antibiotic function of kanamycin is believed to be related to its ability to affect the 30S ribosomal subunit of bacteria, causing frameshift mutations or preventing the translation of RNA. Either frameshift mutations or a lack of RNA translation can lead to a reduction or absence of bacterial protein synthesis and, ultimately, to bacterial death. Unfortunately, kanamycin has been rendered all but obsolete for clinical use due to the emergence of resistant bacteria.

Clearly there exists a need for novel antimicrobials to address the problems of resistant bacteria and fungi, both in human medicine and in crop disease. There is also a clear need for novel antimicrobials, especially antifungals, with reduced toxicity. Furthermore, it would be desirable for new antimicrobial compounds to be selective against either bacteria or fungi, so treatment for one of either bacterial or fungal disease does not contribute to the buildup of antimicrobial resistance in the other. Selective antimicrobial activity is especially desirable for antifungals used to treat crop disease, such as *Fusarium* head blight, due to the possibly large amounts of antimicrobial agent released into the environment when crops are treated. The present invention provides for novel aminoglycoside antimicrobials that are effective, have relatively low levels of toxicity, and are selective against fungal pathogens.

BRIEF SUMMARY OF THE INVENTION

The present invention relates to novel aminoglycoside analogs derived from the parent molecule of kanamycin A. It is an object of the present invention to provide novel aminoglycoside analog compounds with Chemical Formula I as follows:

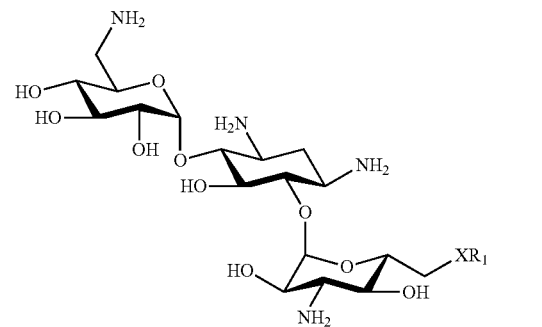

Formula I

Where X is a member selected from the group consisting of O, S, and $NR_2$, $R_1$ is a member selected from the group consisting of $R_3$ (alkyl), $R_3O(CO)$,(alkoxycarbonyl), $R_3NH(CO)$,(alkylaminocarbonyl), $R_3S(O)_2$,(alkylsulfonyl), $R_4S(O)_2$, (phenylsulfonyl), $R_3S(O)$,(alkylsulfinyl), $R_3P(O)_2$, (alkylphosphonyl), $R_3C(O)$ (alkanoyl), and phenyl, wherein phenyl groups may be $C_1$ to $C_6$ alkyl substituted at any ring position; $R_2$ is H or $C_1$ to $C_6$ alkyl, herein $R_3$ is a straight or branched chain $C_4$ to $C_{12}$ alkyl group and wherein $R_4$ is phenyl or $C_1$ to $C_6$ alkyl substituted phenyl.

It is also an object of the present invention to provide novel aminoglycoside analog compounds of Formula I having improved antimicrobial and particularly antifungicidal properties.

A still further object of the present invention is to provide method of synthesizing aminoglycoside analog compounds of Formula I. Yet another object of the present invention is to provide methods of using aminoglycoside analog compounds of Formula I as biocides having improved fungicidal activity.

Without limiting the invention to a any particular method of use, the compounds of the present invention unexpectedly demonstrate increased specificity for fungal pathogens and a lack of activity against some common bacterial pathogens. Other synthetic aminoglycosides and the natural aminoglycosides are either solely bacteriocidal or both bacteriocidal and fungicidal. As a result of its unexpected specificity for fungal pathogens, the compounds of the present invention provides for advantageous treatment of fungal pathogens by not promoting resistance of pathogenic bacteria to traditional aminoglycosides and by not harming or eliminating non-pathogenic bacteria. Various embodiments of the present invention, as well as examples for a method of synthesizing and methods of using the compound of the present invention, are discussed below.

Definitions

Before discussing the present invention in further details, the following terms, when and if used, and conventions will first be defined:

Host: The term "host" is defined herein as any living organism infected or at least somewhat likely of being infected by a fungal pathogen, where said pathogen and any infection caused by said pathogen, or potential infection caused by said pathogen, are susceptible to treatment with one or more of the compounds of Formula I as claimed herein, where said treatment is likely to result in the elimination, avoidance, or alleviation of the infection caused by said pathogen.

The following is in reference to Formulas 1 and 2, Tables 1 and 2 and elsewhere: Unless otherwise designated in Formulas 1 and 2 and Tables 1 and 2, all carbon chains are straight chains, i.e. are n-alkyl or n-alkylene groups and not are branched chains.

When X is O and $R_1$ is $(CO)C_7H_{15}$ the compound is designated herein as K05 and is named 6"-O-octanoylkanamycin A.

When X is O and $R_1$ is $(CO)C_9H_{19}$ the compound is designated herein as K07 and is named 6"-O-decanoylkanamycin A.

When X is NH and $R_1$ is $C_8H_{17}$ the compound is designated herein as K17 and is named 6"-deoxy-6"-octylaminokanamycin A.

When X is S and $R_1$ is $C_8H_{17}$ the compound is designated herein as K18 and is named 6"-deoxy-6"octylthiokanamycin A.

When X is O and $R_1$ is $S(O)_2$p-tolyl the compound is designated herein as K19 and is named 6"-O-toluenesulfonylkanamycin A.

When X is O and $R_1$ is $S(O)_2C_8H_{17}$ the compound is designated herein as K20 and is named 6"-O-octanesulfonylkanamycin A.

When X is O and $R_1$ is $S(O)_2C_6H_{13}$ the compound is designated herein as K22 and is named 6"-O-hexanesulfonylkanamycin A.

For comparative purposes Kanamycin A has the structure:

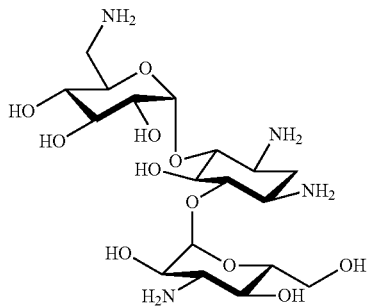

Some or all of the following definitions may also be utilized throughout this disclosure.

Fungal Infection: The term "fungal infection" is defined herein as an association of a fungal organism with a host, whether said association is actual or potential. For example, an actual associate occurs when a fungi is physically present on or within a host. Examples of potential associations include fungi on or within the environment surrounding a host, where the fungi is at least somewhat likely to be actively or passively transferred to the host. Without wishing to further limit the type of associations between a fungal organism and host, examples of the association of the fungal organism with the host include biological associations that may be pathenogenic or non-pathenogenic, parasitic or non-parasitic, symbiotic or non-symbiotic, mutualistic or non-mutualistic, commensal, naturally occurring or man-made, or any other biological interaction.

Host in need thereof: The phrase "host in need thereof" is defined herein as any host associated or potentially associated with a fungal organism, where said host may actually or potentially benefit from elimination, prevention, or alleviation of a fungal infection.

*Fusarium* Head Blight: The phrase "*fusarium* head blight" is defined herein as any fungal disease caused by the fungus *Fusarium graminearum*.

Surfactant: The term "surfactant" is used to indicate the common laboratory surfactant $C_{58}H_{114}O_{26}$. All uses of the term "surfactant" refer to $C_{58}H_{114}O_{26}$, unless otherwise indicated.

Prophylactically: The term "prophylactically" is used herein to refer to the administration of an antimicrobial compound for the prevention of disease.

N/A: As used herein to describe data points, the abbreviation "N/A" means not tested.

Adjuvant: The term "adjuvant" is defined herein as a substance that helps and enhances the pharmacological effect of a drug or increases the ability of an antigen to stimulate the immune system.

Excipient: The term "excipient" is defined herein as an inactive substance used as a carrier for the active ingredients of a medication.

Diluent: The term "diluent" is defined herein as any liquid or solid material used to dilute or carry an active ingredient.

Antifungal Amount or antifungal effective: Unless otherwise specified, the phrases "antifungal amount" or "Antifungal Effective" are used herein to describe an amount of an antifungal agent sufficient to reduce, eliminate, or alleviate a fungal infection or the symptoms of a fungal infection on or within a host.

MIC: The term MIC means the minimal inhibitory concentration or lowest concentration of an antimicrobial that will inhibit the visible growth of a microorganism after 24, 48, or 72 hours of incubation.

Admixed: The term "admixed" is used herein to describe a chemical or compound in a mixture or combination with other chemicals or compounds.

Administering: The term "administering" is defined herein to describe the act of providing, exposing, treating, or in any way physically supplying or applying a chemical or compound to any living organism or inanimate object associated with a living organism, where said organism will actually or potentially benefit for exposure, treatment, supplying or applying of said chemical or compound.

Topical: The term "topical" is defined herein as pertaining to the surface of a body part, surface part of a plant, or surface of an inanimate object or composition, such as soil. For example, in medicine, a topical medication is applied to body surfaces such as the skin or mucous membranes, for example throat, eyes and ears.

Carrier: The term "carrier" is defined herein as any substance that serves to improve the delivery and the effectiveness of a drug or antimicrobial agent and is inclusive of excipients as defined above.

Examples include:

microspheres made of the biodegradable polymer poly (lactic-co-glycolic) acid albumin microspheres;

synthetic polymers (soluble);

protein-DNA complexes;

protein conjugates;

erythrocytes;

nanoparticles; and liposomes

Grain head: The phrase "grain head" as used herein is meant to include both small and large grains.

Warm-blooded animal: Used herein the phrase "warm-blooded animal" means an animal characterized by the maintaining of a relatively constant and warm body temperature independent of environmental temperature; homeothermic.

Certain terms in this application are meant to be interpreted as commonly used in the technical fields of medicine, antimicrobials, and crop disease, as indicated by the context of their use. These terms include spray nozzle, droplet, therapeutically, exterior, spraying, topical, treatment, and prevention.

DETAILED DESCRIPTION OF THE INVENTION

The present invention relates to a antimicrobial compounds comprising Formula I as follows:

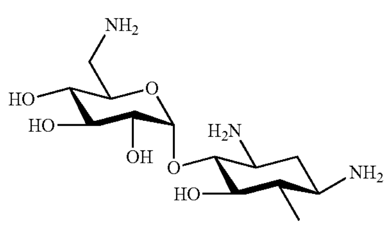

Where X is a member selected from the group consisting of O, S, and $NR_2$, $R_1$ is a member selected from the group consisting of $R_3$ (alkyl), $R_3O(CO)$,(alkoxycarbonyl), $R_3NH(CO)$,(alkylaminocarbonyl), $R_3S(O)_2$, (alkylsulfonyl), $R_4S(O)_2$, (phenylsulfonyl), $R_3S(O)$,(alkylsulfinyl), $R_3P(O)_2$, (alkylphosphonyl), $R_3C(O)$ (alkanoyl), and phenyl, wherein phenyl groups may be $C_1$ to $C_6$ alkyl substituted; $R_2$ is H or $C_1$ to $C_6$ alkyl, $R_3$ is a straight or branched chain $C_4$ to $C_{12}$ alkyl group and $R_4$ is phenyl or $C_1$ to $C_6$ alkyl substituted phenyl.

These compounds are substituted analogs of kanamycin A. The present invention also relates to methods for the synthesis of such analogs and the utilization of them as antifungal agents.

Referring now to the invention in more detail, in Formula 1 there is shown the structure of the compounds related to the present invention. The compounds related to the present invention are analogs of parent molecule kanamycin A. The structure related to the present invention is distinguished from the parent molecule kanamycin A by the presence of functional groups terminating in either an alkyl or phenyl group in the 6 position of ring III.

More specifically, in reference to Formula 1, the functional groups at the 6 position of ring III are identified as $XR_1$ wherein X is a member selected from the group consisting of O, S, and $NR_2$, where $R_2$ is H or $C_1$ to $C_6$ alkyl and $R_1$ is a member selected from the group consisting of $R_3$ (alkyl), $R_3O(CO)$,(alkoxycarbonyl), $R_3NH(CO)$,(alkylaminocarbonyl), $R_3S(O)_2$,(alkylsulfonyl), $R_4S(O)_2$, (phenylsulfonyl), $R_3S(O)$,(alkylsulfinyl), $R_3P(O)_2$,(alkylphosphonyl), $R_3C(O)$ (alkanoyl), and phenyl, wherein phenyl groups may be $C_1$ to $C_6$ alkyl substituted, wherein $R_3$ is a straight or branched chain $C_4$ to $C_{12}$ alkyl group and $R_4$ is phenyl or $C_I$ to $C_6$ alkyl substituted phenyl. Unless otherwise designated $R_3$ is preferable n-alkyl.

In more preferred embodiments X is O or S with O being particularly preferred, but can also be $NR_2$ with $R_2$ being preferably H. $R_1$ is preferably a member selected from the group consisting of $R_3(CO)$(alkyl carbonyl, $R_3SO_2$ (alkylsulfonyl), $R_4(SO)_2$(phenylsulfonyl) and $C_4$ to $C_{12}$ straight or branched chain alkyl. $R_3$ is also $C_4$ to $C_{12}$ straight or branch chain alkyl. $R_4$ is phenyl or $C_I$ to $C_6$ alkyl substituted phenyl. When X is S or $NR_2$, $R_1$ is $C_4$ to $C_{12}$ straight or branch chain alkyl.

EXAMPLES

The following materials and methods were used in either one or more of the examples listed below. Further materials and methods are provided in the description of each example.

Aminoglycosides

All aminoglycosides were kindly provided by the laboratory of Dr. Tom Chang (Department of Chemistry and Biochemistry, Utah State University). For antifungal tests, stock solutions were prepared as 10 mg/mL solutions in water and stored at minus 20° C.

Growth Medium

Fresh potato dextrose broth (PDB)+casamino acids was used throughout. To make 1 l of PDB+casamino acids, 200 g of diced fresh potatoes were boiled in 500 mL of distilled water for 30 min. The broth was filtered through 2 layers of cheese cloth, and the volume was brought up to 1 l. After additions of 20 g of glucose (2%, w/v) and 4 g of casamino acid (0.4%, w/v), the mixture was stirred with a magnetic bar until all solids were dissolved. Then, the medium was sterilized by autoclaving for 30 min. Potato dextrose agar (PDA)+casamino acids medium was prepared with 5% agar and poured into plastic petri plates.

Isolates of *F. graminearum*

Two isolates of F graminearum, B-4-5A and Butte86ADA-11 were obtained from the Small Grain Pathology Program of the University of Minnesota. Both strains were used for MIC tests.

Procedure for In Vitro Antifungal Tests.

In vitro antifungal activities were determined by the general methods of the Clinical and Laboratory Standards Institute (NCCLS. Reference method for broth dilution antifungal susceptibility testing of filamentous fungi. Approved standard M38-A (National Committee for Clinical Laboratory Standards, Wayne, Pa., 2002)). For MIC tests, *Fusarium graminearum* was grown in potato-dextrose+0.4% casamino acids (PDB-CA) medium for 48 h at 28° C. with aerobic shaking. For disk diffusion growth inhibitory assays, various fungal species were inoculated in the middle of PDB-CA agar plate medium surfaces. Sterilized paper disks (0.5 cm diameter) were placed on the inoculated agar medium surfaces equidistant and around the fungal inoculum. Eight μL aliquots of test solutions (10 mg per mL) were applied to the disks, and the plates were incubated for 24 to 48 h at 28° C. before examination of the inhibition patterns. Assays for determination of MICs were conducted in sterile, flat-bottomed 96-well microtiter plates (Corning Costar, Corning, N.Y.) in the range of 500 to 1 μg per mL. Stock solutions of analogs were prepared at concentrations of 2 mg per mL in water. In microtiter plates, 50 μL aliquots of stock solutions were added in the third column and 10 consecutive two-fold serial dilutions were made in each row with sterile distilled water. Then, 40 μL of PDB-CA growth medium and 10 μL aliquots of a 100,000 macroconidia per mL fungal suspension were added to each well. Negative (90 μL of growth medium and 10 μL of water) and positive (90 μL of growth medium and 10 μL of culture or macroconidia) controls were placed in separate wells. The plates were incubated at 28° C. and visually inspected and scored every 24 h. Microbroth dilution assays in a single test were replicated three times, and each test repeated at least twice.

Example 1

6″-O-octanesulfonylkanamycin A (K20)

Formula 2

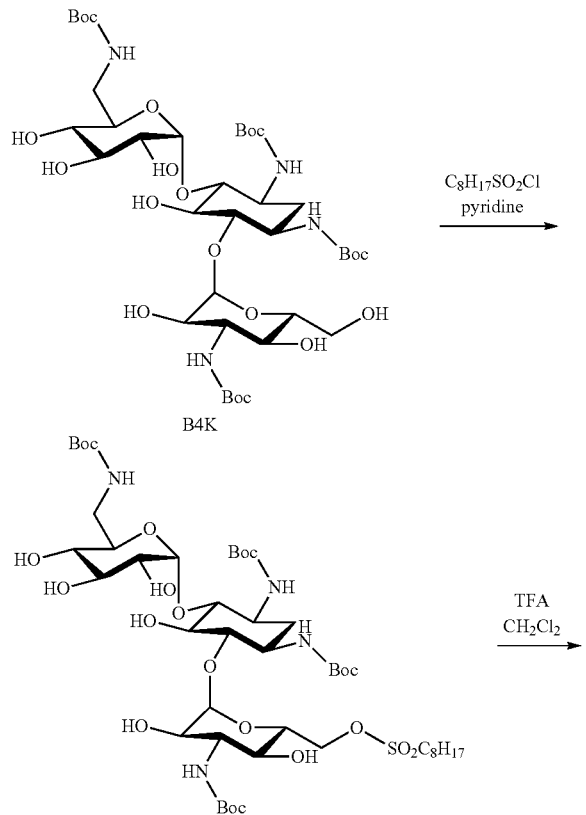

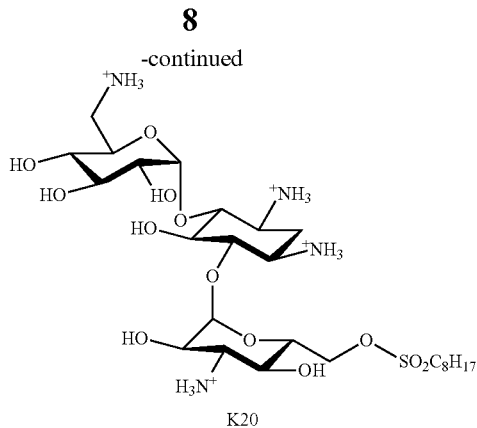

K20

In reference to Formula 2, Tetra-Boc protected Kanamycin (B4K) can be prepared with reported method (J. Med. Chem. 1991, 34, 1468-1476). A solution of B4K (90 g), octanesulfonyl chloride (64 mL) in anhydrous pyridine (800 mL) was stirred at 0° C. overnight allowing the temperature to warm up to room temperature. The clear brownish was stirred for another 6 days at room temperature and one day at 40° C., and then concentrated to oily crude product. Water (500 mL) was added and the mixture was stirred for another day. The mixture was transferred to a separatory funnel with more water and EtOAc (2 L). The organic layer was washed with 0.5 N $HCl_{(aq)}$ (×2) and water. The washing sequence was repeated for 3-4 times. If solid precipitation (mostly unreacted B4K) occurs, the organic layer needs to be filtered first to remove the solid. After completion of the washing, the EtOAc solution was filtered through a Frit funnel and the EtOAC was evaporated. The brownish crude product was treated with a solution of TFA/DCM (1/4) (200 mL). After being stirred overnight, the solvents were removed. Water was added and evaporated to ensure the removal of residual acid. The crude product was dissolve in water and washed with EtOAc till the color in EtOAc become clear. The aqueous solution was evaporated and passed through a column packed with Dowex 1×-8 (Cl-form). After removal of solvent, the desired K20 was afforded as yellowish solid.

Other K20 analogs, i.e. K05, K07, K17, K18, K19 and K22 can be prepared in a similar manner using appropriate reactants in the place of octanesulfonyl chloride. The structure of these analogs and certain biological properties are shown in Table 1.

TABLE 1

Activities of other K compounds

| Code | Structure | MIC (microgram/mL) | Remark |
| --- | --- | --- | --- |
| K05 | 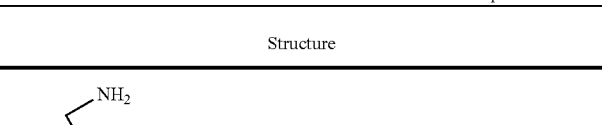 | growth inhibition > 62.5 ug/mL no pigmentation 31.25 ug/mL against *Fusarium graminearum* | |

TABLE 1-continued

Activities of other K compounds

| Code | Structure | MIC (microgram/mL) | Remark |
|------|-----------|--------------------|--------|
| K07 | 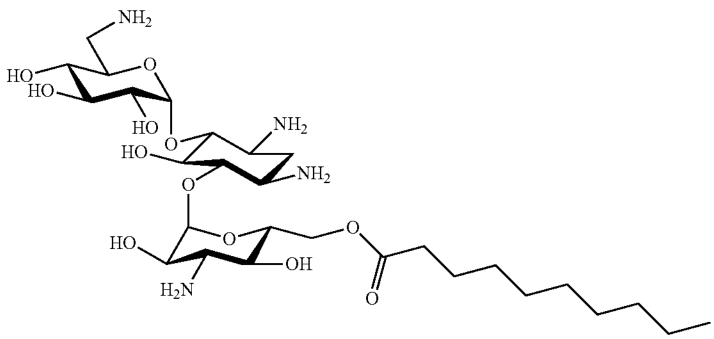 | Similar to K05 | |
| K17 | 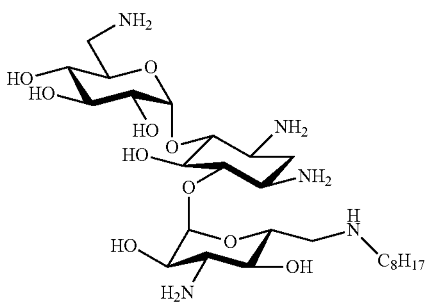 | Not determined. Only inhibition zone assay and not active against *Rhodotorula pilimanae* | The yield is very low. |
| K18 | 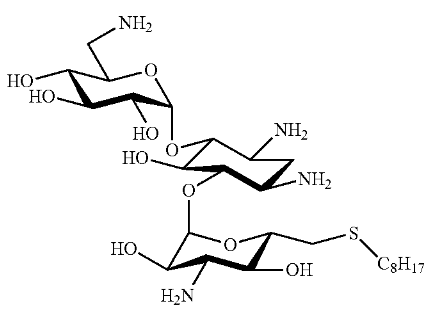 | 16.6 ug/mL against *Fusarium graminearum* 62.5 ug/mL against *Rhodotorula pilimanae* | The yield is very low. |
| K19 | 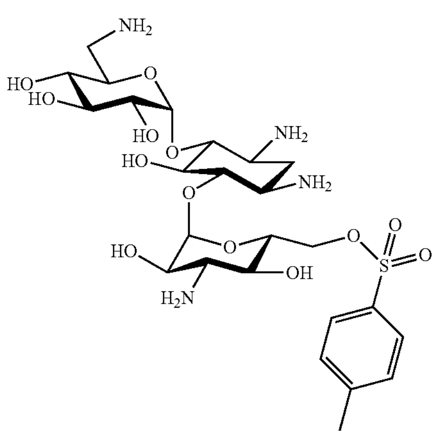 | relatively little but nevertheless some inhibition of *Rhodotorula* | |

TABLE 1-continued

Activities of other K compounds

| Code | Structure | MIC (microgram/mL) | Remark |
|------|-----------|--------------------|--------|
| K22 | 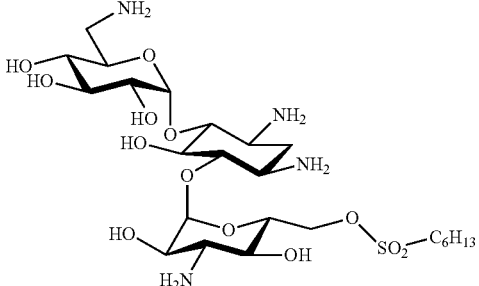 | 31.3 ug/mL against *Fusarium graminearum* | |

Example 2

Relative Growth Inhibitory Activities of K20 Against Bacteria and Fungal Species

TABLE 2

Growth inhibitory activities of K20 against bacteria and fungal species

| Organism | [a]Relative Activity |
|----------|----------------------|
| (Bacteria) | |
| *Staphylococcus aureus* | +++ |
| *Micrococcus luteus* | ++ |
| (Fungi) | |
| *Rhodotorula pilimanae* | + |
| *Typhula ishikarensis* | ++ |
| *Microdochium nevale* | ++ |
| *Fusarium oxysporum* | ++ |
| *Phoma beta* | ++ |
| *Botrytis cinera* | + |
| *Bipolaris* spp. | + |
| *Fusarium graminarum* | [b]+++ |
| *Verticillium* spp. | ++ |

[a]Determined by disk diffusion agar plate assays
+ = some activity
++ = moderate activity
+++ = considerable activity
[b]Separate microbroth dilution growth inhibition tests show MICs of 7.8-15.6 microgram mL$^{-1}$ Referring now to Table 2 there is shown the relative growth inhibitory activities of K20 against various species of bacteria and fungi as determined by disk diffusion agar plate assays. While K20 showed both antibacterial and antifungal activity what is of considerable importance is the activity shown against *Fusarium graminarum*. *Fusarium graminarum* is a fungus that infects wheat and the disease is also known as head scab or *fusarium* head blight and is a serious deterrent to the harvesting of good quality wheat and often results in farmers being forced to discard their crop. As noted in Table 2 the testing of K20 against *Fusarium* graminarum resulted in MIC's of between 7.8 and 15.6 μg/mL.

Example 3

Antifungal Activities of Other K Compounds Against *Fusarium graminearum* and/or *Rhodotorula pilimanae*

Referring now to Table 1 there is shown the relative growth inhibitory activities of K20 against *Fusarium graminearum* and/or *Rhodotorula pilimanae* as determined by disk diffusion agar plate assays. The alkylsulfonyl, alkylcarbonyl, and alkylthio derivatives of kanamycin A were shown to be more active than the alkylamino and toluene (p-methylphenyl) derivatives which, nevertheless shows some antifungal activity.

Example 4

Selective Antimicrobial Activity of K20

The MICs of K20 were determined for selected bacterial pathogens. For purposes of the experiments discussed in this paragraph, the MIC is defined as the lowest concentration of compound needed to inhibit the growth of bacteria. A solution of a selected bacterium was inoculated Trypticase Soy broth at 35° C. and incubated for 1-2 hours. Following incubation, the bacterial concentrations were determined, and diluted with broth, if necessary, to an absorption value of 0.08 to 0.1 at 625 nm. The adjusted inoculated medium (100 μL) was diluted with 10 mL broth, and then applied to a 96-well microtilter plate (50 μL). A series of solutions (50 μL each in 2-fold dilution) of K20 was added to the testing wells. The 96-well plate was incubated at 35° C. for 12-18 hrs. The MIC results were repeated at least three times. MIC values (in tg/mL) for K20 against the following bacteria are as follows: 250 for *Escherichia coli* strain B, 62.5 for *Micrococcus luteus*. Corresponding MIC values for kanamycin A and B were 0.98 μg/mL for *Micrococcus luteus* and 1.95 μg/mL for *Escherichia coli*. The MIC values determined for K20 exceed the values that typically prompt consideration of candidate compounds as effective antibacterial antibiotics (<16 pg/mL) whereas MIC values for kanamycin A and B demonstrated effective antibacterial activity.

In summary, the amimoglycoside analogs of the present invention demonstrate insufficient or no antibacterial activity and is structurally distinct from kanamycin A due to the presence of a carbon alkyl chain or aryl ring on ring III. The carbon alkyl chain or aryl ring on ring III, absent on the parent molecule kanamycin A, is the structural feature of the present invention most likely responsible for the novel antifungal activity of the present invention. The fungal specificity of the present invention will benefit crop protection strategies because use of the present invention will not promote bacterial resistance, whereas conventional aminoglycosides do promote bacterial resistance.

One preferred embodiment of the present invention is the treatment of fungal infection in a host in need thereof, where the elimination or reduction of bacteria associated with said host is undesirable. Without wishing to limit the scope of the invention in any way, one such use could occur in human or non-human mammals, where treatment of a fungal infection with and aminoglycoside of the invention such as K20 would eliminate or alleviate the fungal infection, but not affect the integrity of the intestinal flora of the host. Again, without limiting the invention, a second example is the treatment or prevention of fungal disease in a host crop, where it is undesirable to affect the diversity or abundance of bacteria of said host crop.

In broad embodiment, the present invention is drawn to novel antifungal compounds, a method to synthesize said novel antifungal compounds, and methods to use said novel antifungal compounds to treat humans, animals, soil, or plants to eliminate fungal growth and activity. In one broad embodiment, the structure related to the present invention is derived from a parent aminoglycoside molecule other than kanamycin A that is capable of being modified by the addition of a variety of substituents on ring III equivalent of the ring III of kanamycin A. Particularly preferred is the addition of a carbon alkyl chain as designated herein on ring III. In yet another broad embodiment the present invention is derived from the parent aminoglycoside molecule by the synthesis method shown herein, but the substituent, such as the carbon alkyl chain on ring III of the structure related to the present invention varies in the number of carbon atoms and hydrogen atoms. In still yet another broad embodiment, the present invention is used to treat a variety of fungal pathogens related to human, crop, or animal disease. In further broad embodiments, the compound of the present invention is administered by spraying, direct injection, topical application, ingestion (including pharmaceutical compositions the include the structure related to the present invention), or by inclusion in the water supply, to either a human, an animal, or a crop immediately threatened by, or potentially threatened by, a fungal pathogen, where fungal pathogen is causing or may cause fungal disease, and administration of the compounds of the present invention will reduce, eliminate, or avoid fungal disease.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed. Such embodiments may encompass different means of applying the compounds of the present invention, including, but not limited to, spraying, topical application, or injection. Various embodiments may also include the treatment different kinds of hosts susceptible to fungal infections. Types of hosts can include, but are not limited to, warm-blooded animals (including humans and other mammals), plants, fish, or bacterial cultures.

The invention claimed is:

1. A fungicidal aminoglycoside compound, or a salt thereof, having the formula:

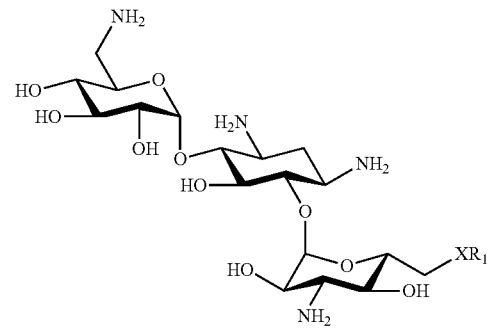

wherein:
X is a member selected from the group consisting of O and S;
$R^1$ is a member selected from the group consisting of $—R^3$, $—C(O)OR^3$, $—S(O)_2R^3$, $—S(O)_2R^4$, $—S(O)R^3$, $—P(O)_2R^3$, and phenyl, wherein said phenyl is $C_1$ to $C_6$ alkyl substituted;
$R^3$ is a straight or branched chain $C_6$ to $C_{12}$ alkyl group; and
$R^4$ is phenyl or $C_1$ to $C_6$ alkyl substituted phenyl.

2. The compound according to claim 1, wherein X is O.

3. The compound according to claim 1, wherein X is S.

4. The compound according to claim 1, wherein:
$R^1$ is a member selected from the group consisting of $—S(O)_2R^3$ and $—S(O)_2R^4$,
$R^3$ is $C_6$ to $C_{12}$ straight or branched chain alkyl, and
$R^4$ is phenyl or $C_1$ to $C_6$ alkyl substituted phenyl.

5. A fungicidal aminoglycoside compound, or a salt thereof, having the formula:

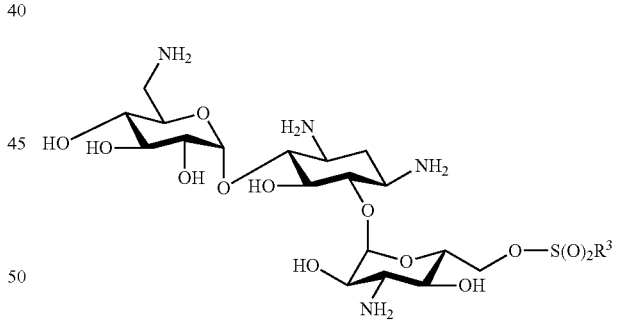

wherein $R^3$ is a straight or branched chain $C_4$ to $C_{12}$ alkyl group.

6. The compound according to claim 5, wherein $R^3$ is $C_8H_{17}$.

7. The compound according to claim 5, wherein $R^3$ is $C_6H_{13}$.

8. The compound according to claim 1, wherein X is O and $R^1$ is $—S(O)_2R^4$.

9. The compound according to claim 8, wherein $R^4$ is p-tolyl.

10. A method of treating a fungal infection which comprises administering to a host in need thereof an effective amount of an aminoglycoside compound having the formula:

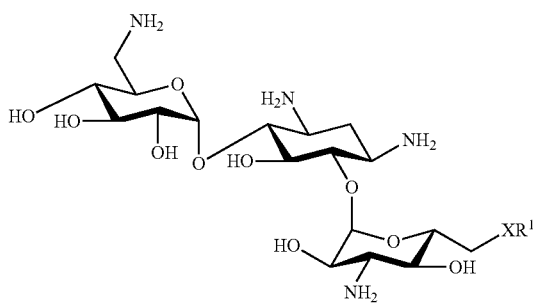

wherein:
X is a member selected from the group consisting of O and S;
$R^1$ is a member selected from the group consisting of —$R^3$, —C(O)O$R^3$, —S(O)$_2R^3$, —S(O)$_2R^4$, —S(O)$R^3$, —P(O)$_2R^3$, and phenyl, wherein said phenyl is $C_1$ to $C_6$ alkyl substituted;
$R^3$ is a straight or branched chain $C_6$ to $C_{12}$ alkyl group; and
$R^4$ is phenyl or $C_1$ to $C_6$ alkyl substituted phenyl.

11. The compound according to claim 10, wherein:
$R^1$ is a member selected from the group consisting of —S(O)$_2R^3$ and —S(O)$_2R^4$,
$R^3$ is $C_6$ to $C_{12}$ straight or branched chain alkyl, and
$R^4$ is phenyl or $C_1$ to $C_6$ alkyl substituted phenyl.

12. The method according to claim 10, wherein X is O and $R^1$ is —S(O)$_2R^3$.

13. The method according to claim 12, wherein $R^3$ is $C_6H_{13}$.

14. The method according to claim 12, wherein $R^3$ is $C_8H_{17}$.

15. The method according to claim 10, wherein said host in need thereof is a plant.

16. The method according to claim 10, wherein said fungal infection is caused by *F. graminearum*.

17. The method according to claim 15, wherein a grain head portion of said plant is treated.

18. The method according to claim 10, wherein said host in need thereof is a warm blooded animal.

* * * * *